(12) United States Patent
Park

(10) Patent No.: US 6,223,751 B1
(45) Date of Patent: May 1, 2001

(54) INCONTINENCE DEVICE

(76) Inventor: Douglas K Park, 62-10 Woodside Ave. #410, Woodside, NY (US) 11377

( * ) Notice: Subject to any disclaimer, the term of this patent is extended or adjusted under 35 U.S.C. 154(b) by 0 days.

(21) Appl. No.: 09/477,007

(22) Filed: Jan. 3, 2000

(51) Int. Cl.[7] .................................................. A61F 5/48
(52) U.S. Cl. .................. 128/885; 604/349; 128/DIG. 25
(58) Field of Search ..................... 604/349–353; 128/882, DIG. 25; 600/29

(56) References Cited

U.S. PATENT DOCUMENTS

| | | | |
|---|---|---|---|
| 2,873,740 | * | 2/1959 | WainWright ............ 604/349 |
| 3,559,651 | * | 2/1971 | Moss ..................... 604/349 |
| 5,593,389 | * | 1/1997 | Chang .................... 604/349 |

FOREIGN PATENT DOCUMENTS

0657004 * 2/1963 (CA) ............................ 604/349

\* cited by examiner

*Primary Examiner*—Michael A. Brown
(74) *Attorney, Agent, or Firm*—Michael I. Kroll

(57) ABSTRACT

The present invention 10 discloses a device for use by patients having incontinence. Disclosed is a cup 16 for receiving the penis of the user. The cup 16 contains a urine pad 30 for absorbing urine which cup is supported in the proper position by a waist belt 22 with buckle 24 having additional straps 12 with buckles 14 for attachment of the cup 16. Clip strings 18 having clip attachment members 20 thereon connect the straps to eyelets 26 disposed on the top rim of the cup 18. The cup 18 is divided into an upper 15 and lower 19 chamber by a funnel-like partition 23 having a drain hole 38 therein. The urine pad 30 is located in the lower chamber 19 of the housing.

1 Claim, 6 Drawing Sheets

INCONTINENCE DEVICE

BACKGROUND OF THE INVENTION

1. Field of the Invention

The present invention relates generally to absorbent urine pads and, more specifically, to a urine collection device having disposable absorbent pads contained therein. The present device is comprised of a waist belt assembly having and a urine collection member. The urine collection member is comprised of a cup having a cover element which has an aperture for insertion of and retention of a penis. Further the cup has an absorbent pad contained therein which can be selectively discarded and replaced. As the urine is discharged from the penis to the holding cup, the urine is funneled into the lower compartment in which the urine is than absorbed by the urine pads. The urine collecting and absorbing cup also comprises four loop type eyelets located at the top of the cup's rim providing means for selectively attaching/detaching the cup member from the waist harness using the harnesses four rubber clips.

The urine collection device can be used by patients of prostate or urine path surgery. The harness assembly is comprised of adjustable buckles located on the main waist belt and two waist straps. The urine collecting and absorbing harness assembly can be manufactured using elastic material for stretch and comfort to wearer. The urine collection member may be removed and replaced by unhooking the rubber holding clips, located at the rim of the urine cup. Once the four clips are removed from the urine cup, the cup is free to be replaced. The harness device remains on the patient during the removal and replacement of urine absorbent cups. The urine collecting and absorbing cups are disposable and replaced with a new cup as required. The present invention is applicable to any kind of patient, with physical injuries requiring a urine discharge collecting and absorbing device, and will contribute to the care and sanitary conditions without causing leaking or spilling of absorbed and collected urine. The urine collection and absorbent device of the present invention provides means for storage of expelled urine prior to ultimate disposal.

2. Description of the Prior Art

There are other urine absorbent device designed for the absorbing of urine discharge. Typical of these is U.S. Pat. No. 4,886,510 issued to Iwao Matsuura on Dec. 12, 1989.

Another patent was issued to Leopoldine Walsh et al. on Feb. 19, 1991 as U.S. Pat. No. 4,994,051. Yet another U.S. Pat. No. 5,645,541 was issued to Richard Bouser on Jul. 8, 1997 and still yet another was issued on Jul. 22, 1997 to Morton Cohen as U.S. Pat. No. 5,649,913.

Another patent was issued to James Marran on Aug. 11, 1998 as U.S. Pat. No. 5,792,127. Yet another U.S. Pat. No. 5,792,132 was issued to Lucia Garcia on Aug. 11, 1998.

U.S. Pat. No. 4,886,510

Inventor: Iwao Matsuura

Issued: Dec. 12, 1989

A urine-collecting device comprises a urine collecting bag having an opening for inserting a penis therethrough, the opening being made on one side surface of the bag; a film for preventing a back flow of urine having a hole with a diameter being smaller then that of the opening; and a flexible sheet-like flange having a hole corresponding to the opening, wherein the film and flange are fixed to the bag in this order in a manner such that the holes of the film and flange correspond to the opening of the bag, and a circumstance of the hole of the flange is fixed to the bag. Further, the film has a thin portion at the center and a thick portion there around and the penis is softly sealed by the inner edge of the thin portion. According to a device of the present invention, the device is applicable to any kind of patient, does not either cause a feeling of physical disorder or injure a penis, enables a bedridden old man or sick person to urinate while lying in order to contribute to the care thereof, and can be used sanitarily without causing a leak of urine.

U.S. Pat. No. 4,994,051

Inventor: Leopoldine Walsh

Issued: Feb. 19, 1991

An external catheter system for males including a waist belt assembly, a genital sheath having a scrotum bar, and a urine collector, wherein the sheath and urine collector are interconnected by a length of flexible tubing. The urine collector provides means for collection of expelled urine and means to stage and treat expelled urine prior to ultimate disposal.

U.S. Pat. No. 5.645.541

Inventor: Richard E. Bouser

Issued: Jul. 8, 1997

A urinal device is disclosed for the reception therein of a user's penis. The device includes a support worn by the user for supporting the device relative to the user. A collar is secured to the support for the reception therein of the users penis. The arrangement is such that in use of the device, the users penis is inserted through the collar. The collar has a first and second end. A flexible tubular portion is provided for sealing the device relative to the users penis, the tubular portion having a first and second extremity. The first extremity engages the first end of the collar and the second extremity sealingly cooperates with the users penis. A collecting device sealingly cooperates with the second end of the collar, the arrangement being such that in the use of the device, the users penis is sealingly supported by the tubular portion so that the users penis is disposed within the collar.

U.S. Pat. No. 5,649,913

Inventor: Morton H. Cohen

Issued: Jul. 22, 1997

Mens boxer shorts for incontinence. The front panel thereof has a bottom which is turned upwardly to form a pocket for receiving and storing urine. A ring, of elastic or soft cloth material, is attached to the top of the pocket for encircling a mans penis to direct the flow of urine into the pocket.

U.S. Pat. No. 5,792,127

Inventor: James E. Marran

Issued: Aug. 11, 1998

A urine collection and drainage device comprising a chamber that contains a baffle. The device minimizes noises generated from sloshing urine in the chamber. Furthermore, when secured in a horizontal orientation relative to an individuals leg, the device is completely concealed from view by others while worn under shorts, short skits or swimming trunks. Thus, the device collects urine such that it baffles any sloshing noises that emanate from the chamber and is completely from view when worn under summer or sport apparel.

U.S. Pat. No. Des. 5,792,132

Inventor: Lucia Marta Garcia

Issued: Aug. 11 1998

This United States patent discloses an ornamental design for a incontinence device as illustrated in the drawings of the patent. An incontinence diaper system for providing an incontinence diaper with a drainage system to reduce urine excrement with the incontinence diaper. The incontinence diaper system includes a diaper having a drain aperture, an internal liner juxtaposed to the diaper having a funnel aperture into one side, a drain funnel secured within the funnel aperture to collect the urine absorbed by the interior liner, a tubing coupled to a drain funnel opposite of the funnel aperture, and a reservoir coupled to the tubing opposite the drain funnel to store the collected urine which flows through the tubing. For males, an elongated tapering tube having a bulbous enlarged end for coupling to the penis.

While these incontinence devices may be suitable for the purposes for which they were designed, they would not be as suitable for the purposes of the present invention, as hereinafter described.

SUMMARY OF THE PRESENT INVENTION

The present invention discloses a device for use by patients having incontinence. Disclosed is a cup for receiving the penis of the user. The cup contains a urine pad for absorbing urine which cup is supported in the proper position by a waist belt with buckle having additional straps with buckles for attachment to the cup. Clip strings having clip attachment members thereon connect the straps to eyelets disposed on the top rim of the cup. The cup is divided into an upper and lower chamber by a partition having a drain hole therein. The urine pad is located in the lower chamber of the housing.

A primary object of the present invention is to provide an incontinence device that collects and absorbs urine.

Another object of the present invention is to provide an incontinence device that collects and absorbs urine comprising a urine-collecting cup.

Yet another object of the present invention is to provide an incontinence device that collects and absorbs urine comprising a urine collecting cup, a thin rubber, latex or water proof material having an opening for penis placement and penis holding.

Still yet another object of the present invention is to provide an incontinence device that collects and absorbs urine comprising a urine collecting cup, a thin rubber, latex or water proof material having an opening for penis placement and holding, also containing absorbing pads in the lower housing of the cup.

Yet another object of the present invention is to provide an incontinence device that collects and absorbs urine comprising a urine collecting cup, a thin rubber, latex or water proof material having an opening for penis placement and holding, also containing absorbing pads in the lower housing of the cup. The present invention also consists of a harness assembly having clip attachment and holding means for the urine collection member.

Additional objects of the present invention will appear as the description proceeds.

The present invention overcomes the shortcomings of the prior art by providing an incontinence device that collects and absorbs urine comprising a urine collection cup, a thin rubber, latex or water proof material having an opening for penis placement and holding. Also containing absorbing pads in the lower housing of the cup and a harness assembly having clip means for attaching and holding the urine collection member. The harness assembly has an adjustable waist belt and a number of straps.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
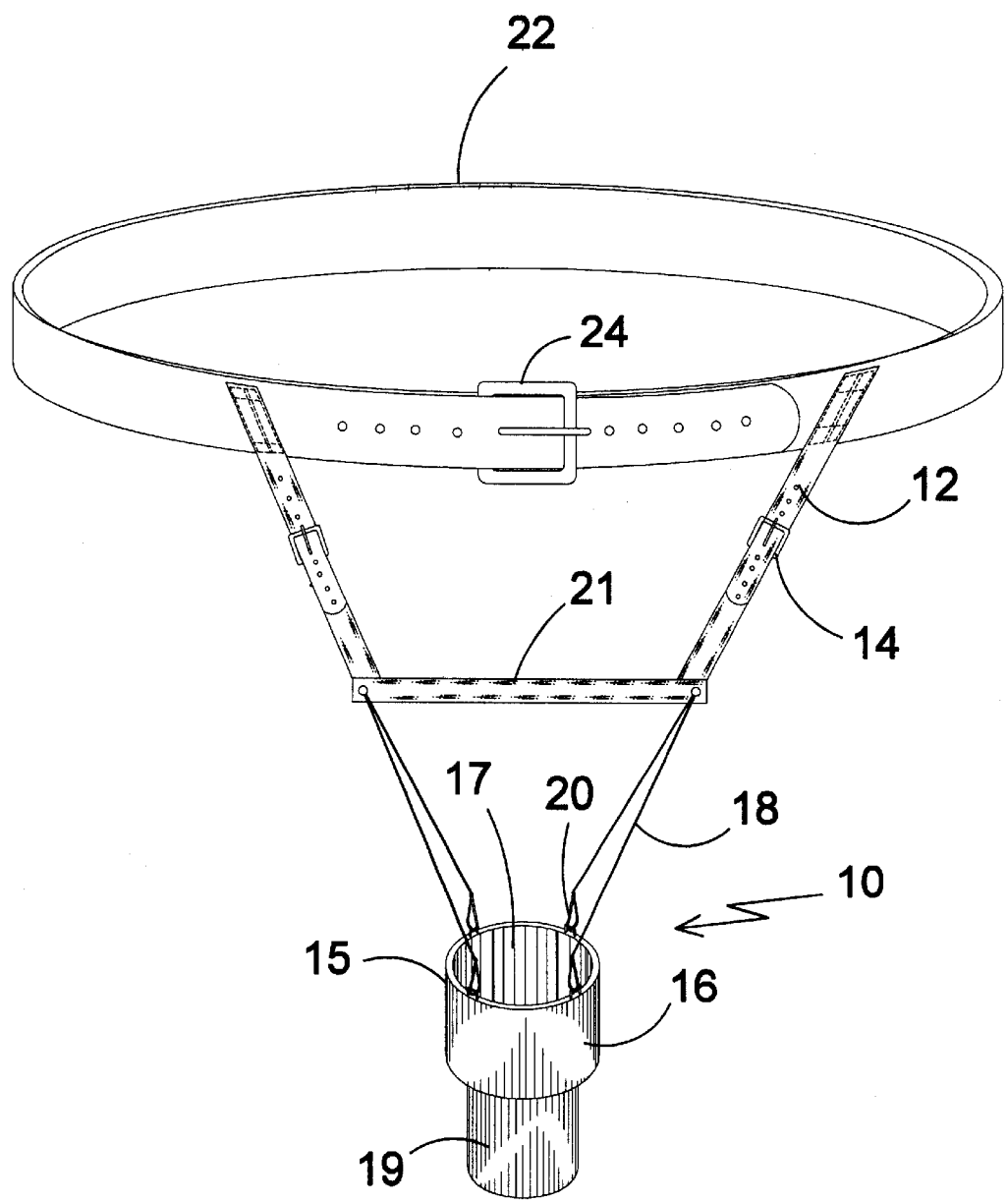
FIG. 1 is a perspective view of the present invention, incontinence device in its fill assembly. Shown are the adjustable straps and buckles of the harness device attached to the urine-absorbing cup by means of clip strings and clip attachments.

With regard to reference numerals used, the following numbering is used throughout the drawings.

10 present invention
12 straps
14 buckles
15 upper part of cup
16 cup
17 opening in upper cup
18 clip strings
19 lower part of cup
20 clip attachments
21 cross-strap member
22 waist belt
23 bottom of upper part of cup/partition
24 waist belt buckle
26 eyelets
28 rim of cup
30 urine pad
32 direction arrow
34 urine
36 lower housing
38 drain hole

BRIEF DESCRIPTION OF THE PREFERRED EMBODIMENT(S)

In order that the invention may be more fully understood, it will now be described, by way of example, with reference to the accompanying drawings in which FIGS. 1 through 6 illustrate the present invention being a device for incontinence.

Turning to FIG. 1, shown therein is a perspective view of the present invention 10, being an incontinence device in its full assembly. The present invention 10 is comprised of a waist belt 22 having a urine collection member 16 attached thereto. The urine collection member 16 is comprised of a cup 16 having an upper portion 15 which has an opening 17 therein for insertion of and retention of the penis of the user. Further the cup 16 has an absorbent pad (not shown) contained in a lower part 19 which pad can be selectively discarded and replaced. Shown are the adjustable straps 12 and buckles 14 of the harness device attached to the urine absorbing cup 16 by means of clip strings 18 and clip attachments 20. Also shown is the waist belt 22 and buckle 24 along with a cross-strap member 21 which connects the lower ends of straps 12.

Figure 2:
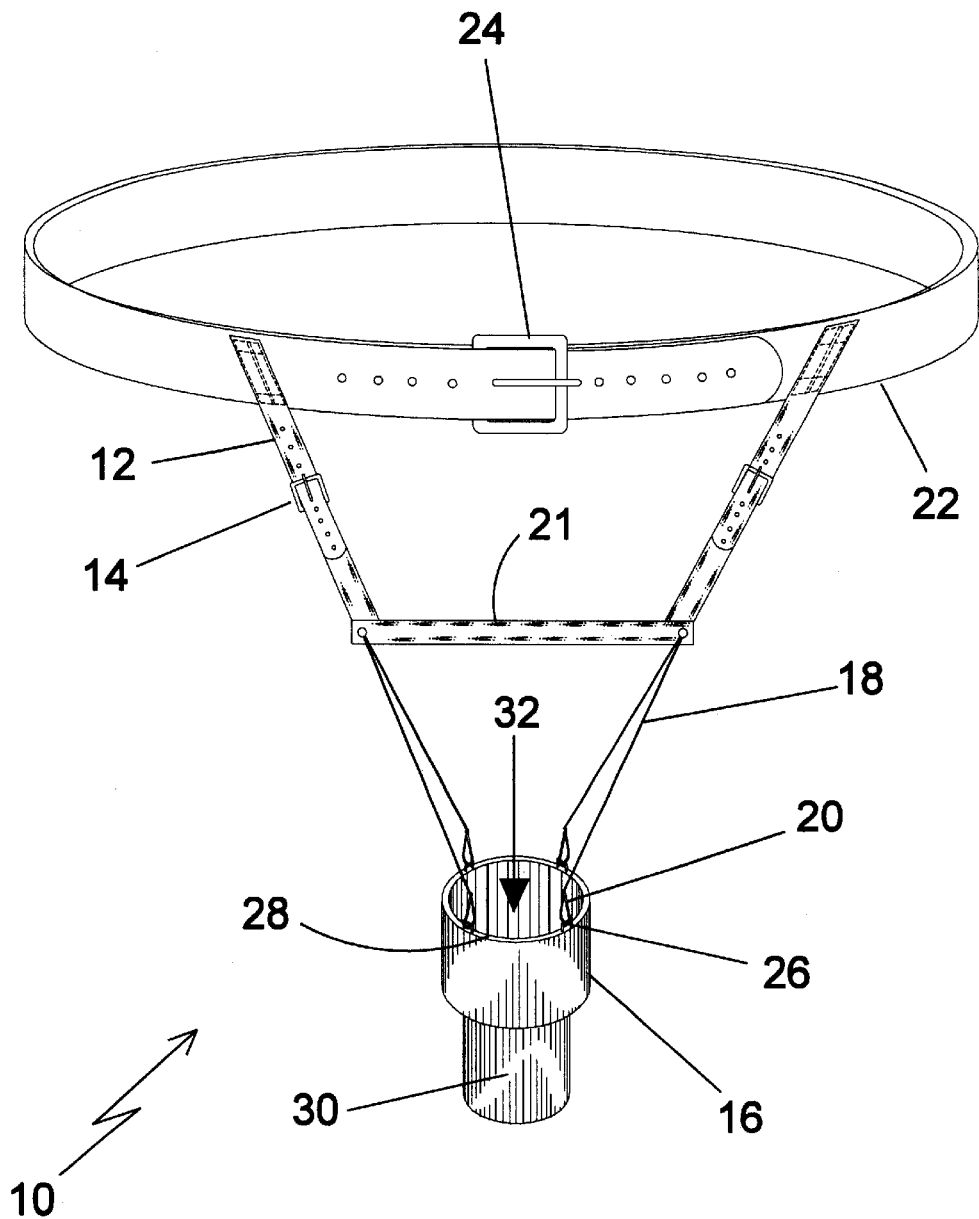
FIG. 2 is a perspective view of the present invention, continence device in its full assembly. Shown, the adjustable waist strap and buckles attached to cup strings and clips in which attach to eyelets at the rim of the urine cup.

Turning to FIG. 2, shown therein is a perspective view of the present invention 10, being an continence device in its full assembly. Shown is the adjustable waist strap 22 and buckle 24. Also shown are straps 12 and buckles 14 attached to cup strings 18 and clips 20 which attach to eyelets 26 at the rim 28 of the urine cup 16. The cup 16 has an absorbent urine pad 30 contained therein and has a cavity therein for receiving the penis as shown by direction arrow 32. The harness assembly is comprised of adjustable buckles 14 connected on the main waist belt 22 and two waist straps 12. The urine collecting and absorbing harness assembly can be manufactured using elastic material for stretch and comfort to the wearer. The urine collection member may be removed and replaced by unhooking the rubber holding clips 20, located at the rim 28 of the urine cup 16. Once the four clips 20 are removed from the urine cup 16, the cup is free to be replaced. The harness device remains on the patient during the removal and replacement of urine absorbent cups 16. The urine collecting and absorbing cups 16 are disposable and replaced with a new cup as required. The urine collection and absorbent device of the present invention 10 provides means for storage of expelled urine prior to ultimate disposal. Other elements previously disclosed are also shown.

Figure 3:
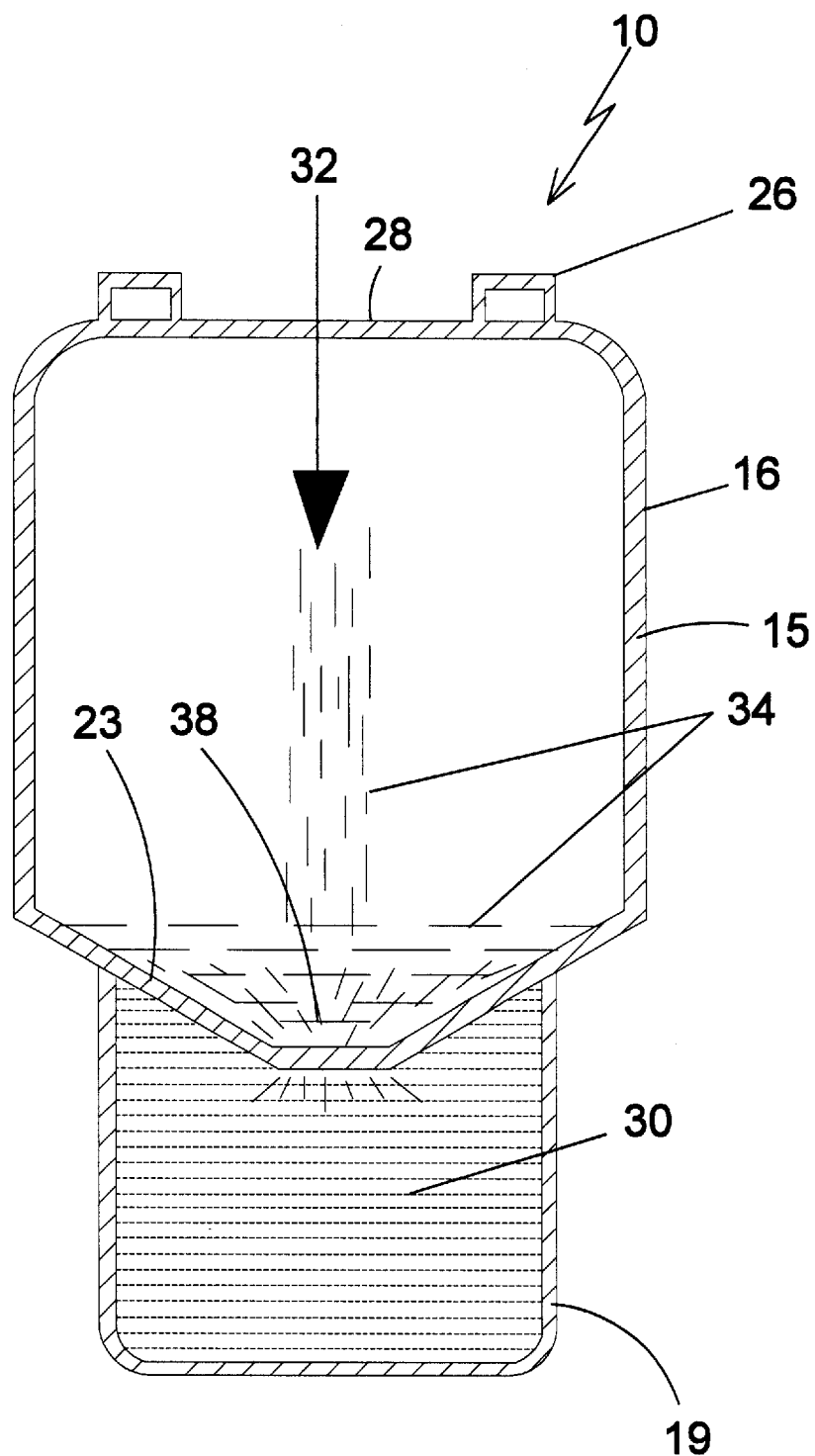
FIG. 3 is a sectional view of the present invention depicting urine flow from the user, being funneled into the absorbent pads located in the lower housing of the urine cup of the present invention.

Turning to FIG. 3, shown therein is a sectional view of the present invention 10 depicting urine flow 34 from the user, being funneled through hole 38 into the absorbent pads 30 located in the lower portion 19 of the urine cup 16 of the present invention 10. The upper portion of cup has funnel-like inwardly sloping sides formed on its bottom 23. Eyelets 26 for receiving the clip attachments are also shown. Direction arrow 32 which represents the penis position is also shown. As the urine 34 is discharged from the penis to the holding cup 16, the urine is funneled into the lower compartment 19 where he urine 34 is then absorbed by the urine pads 30. The urine collecting and absorbing cup 16 also comprises four loop type eyelets 26 located at the top of the cup's rim 28 providing means for selectively attaching/detaching the cup member 16 from the waist harness using the four rubber clips.

Figure 4:
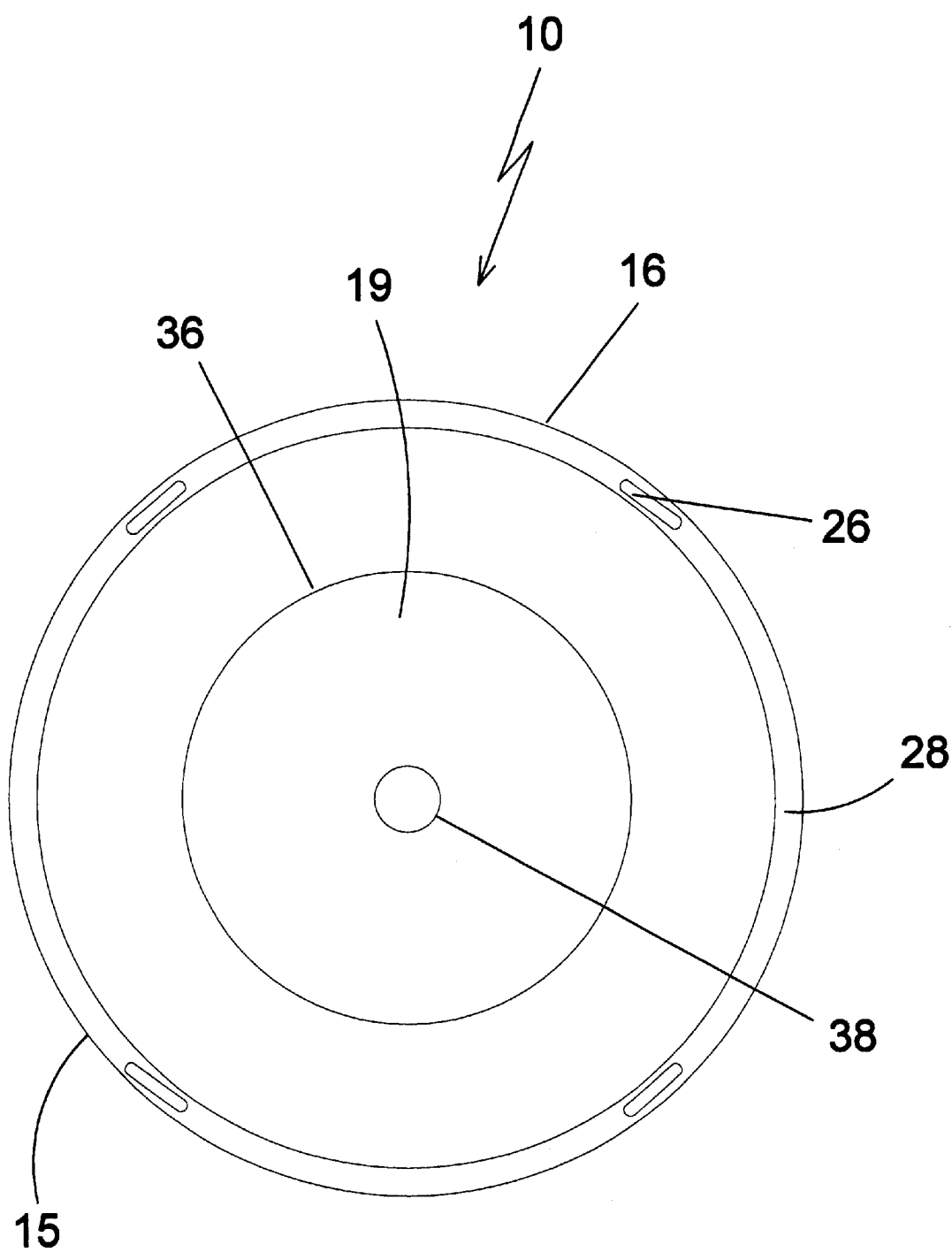
FIG. 4 is a top view of the urine cup of the present invention. Shown are the clip eyes in which the harness of the present invention is secured to the urine cup by means of clips. Also depicted is the lower housing of the urine cup containing urine absorbent pads. Also shown, the funneled drain hole in which urine drains from the upper housing of the present invention into the lower housing of the present invention for absorption.

Turning to FIG. 4, shown therein is a top view of the rim 28 of the urine cup 16 of the present invention 10. Shown are the clip eyes 26 in which the harness of the present invention is secured to the urine cup 16 by means of clips. Also depicted is the top of the lower housing 19 of the urine cup 16 containing urine absorbent pads 36. Also shown is the funneled drain hole 38 through which urine drains from the upper housing 15 of the present invention into the lower housing 19 of the present invention for absorption.

Figure 5:
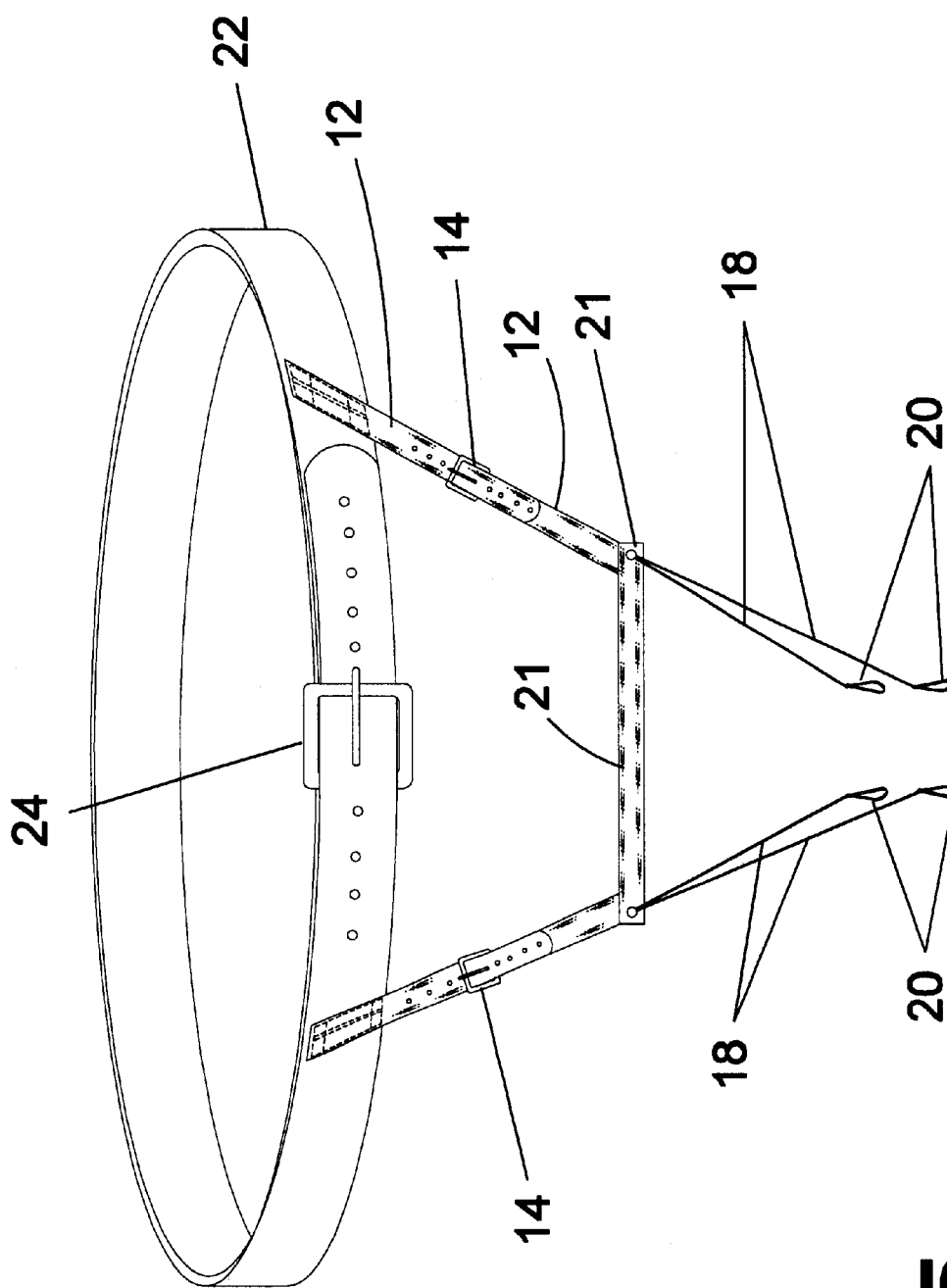
FIG. 5 is a perspective view of the harness system of the present invention. Shown, the elastic waistband and adjustable straps, buckles and cup strings and clips in which attach to the urine cup of the present invention.

Turning to FIG. 5, shown therein is a perspective view of the harness system of the present invention. Shown is the elastic waist band 22 and adjustable straps 12, buckles 14, 24, cross-strap 21 and cup strings 18 and clips 20 which attach to the urine cup (not shown) of the present invention.

Figure 6:
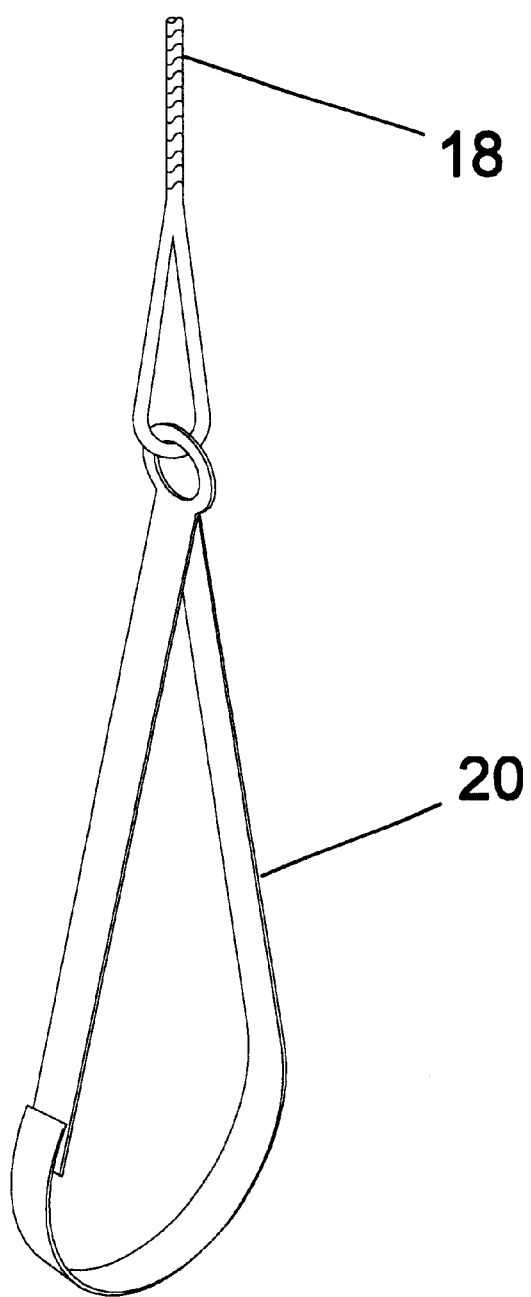
FIG. 6 is a perspective view depicting the clip of the present invention. The clips are attached to clip strings in which are connected to the main harness of the present invention. The clips function is to attach and detach the waist harness to and from the urine cup of the present invention, as means to stage and treat expelled urine prior to ultimate disposal.

Turning to FIG. 6, shown therein is a perspective view depicting the clip 20 of the present invention. The spring-tensioned safety clips 20 are attached to clip strings 18 which are connected to the main harness of the present invention. The clips 20 function to attach and detach the waist harness to and from the urine cup of the present invention, as a means to stage and treat expelled urine prior to ultimate disposal.

What is claimed to be new and desired to be protected by Letters Patent is set forth in the appended claims:

I claim:

1. An apparatus for use by a male user having incontinence, the apparatus for receiving the penis of the male, comprising:

a) a cup member for receiving the penis;
b) said cup member having a first upper housing with a cylindrical wall circular in cross section for receiving the penis and a second lower cylindrical housing circular in cross section, the diameter of said lower housing being less than the diameter of said upper housing;
c) said upper housing having a conical bottom extending into a top opening of said lower housing forming a partition separating said first upper housing and said second lower housing, said partition having a drain hole therein, an upper rim of said lower housing being in contact with said conical bottom along a line below the bottom of the cylindrical wall of said upper housing;

d) a urine absorption pad contained in said second lower housing;

e) means for attaching said cup member to the user comprising a waist belt with a buckle, a pair of downwardly extending adjustable belts attached at top ends thereof to said waist belt, a cross-strap member connecting lower ends of said pair of downwardly extending belts, and a pair of downwardly extending strings attached at their upper ends to the lower end of each of said downwardly extending belts where said cross-strap member is attached;

f) a spring-tensioned safety clip mounted on a bottom end of each of said strings; and g) a plurality of spaced, integrally molded eyelets mounted along an upper rim of said upper housing for engagement by said safety clips to support said cup member on said user.

* * * * *